United States Patent [19]
Frentzen et al.

[11] Patent Number: 5,693,817
[45] Date of Patent: Dec. 2, 1997

[54] SOLVENT-FREE PROCESS FOR PREPARING 4-AMINO-2,2,6,6-TETRAMETHYLPIPERIDINE

[75] Inventors: Stefan Frentzen, Raesfeld; Elmhart Neuber, Haltern; Gerhard Thelen, Nottuln, all of Germany

[73] Assignee: Huels Aktiengesellschaft, Marl, Germany

[21] Appl. No.: 566,993

[22] Filed: Dec. 4, 1995

[30] Foreign Application Priority Data

Dec. 2, 1994 [DE] Germany .................. 44 42 990.8

[51] Int. Cl.[6] .................................. C07D 211/56
[52] U.S. Cl. .................................. 546/244
[58] Field of Search .................................. 546/244

[56] References Cited

U.S. PATENT DOCUMENTS 5,395,972  3/1995  Furutani et al. .................. 564/446

OTHER PUBLICATIONS

CA 122:160152, Furutani et al., 1995.

CA 109:6422, Popava et al., 1988.

CA 107: 39635, Takahashi et al., 1987.

*Primary Examiner*—Jane Fan
*Attorney, Agent, or Firm*—Oblon, Spivak, McClelland, Maier & Neustadt, P.C.

[57] ABSTRACT

A process for preparing 4-amino 2,2,6,6-tetramethylpiperidine (TAD) from 2,2,6,6-tetramethylpiperidone (TAA), ammonia and hydrogen using a cobalt or nickel catalyst on a support which allows the omission of any added solvent, and provides substantially simplified work-up and increased space-time yields by significantly reducing the amounts of excess ammonia and catalyst needed to accomplish the reaction.

11 Claims, No Drawings

SOLVENT-FREE PROCESS FOR PREPARING 4-AMINO-2,2,6,6-TETRAMETHYLPIPERIDINE

BACKGROUND OF THE INVENTION

1. Field of the Invention

The present invention relates to a substantially solvent-free process for preparing 4-amino 2,2,6,6-tetramethylpiperidine (also known as triacetonediamine or TAD) from 2,2,6,6-tetramethylpiperidone ( also known as triacetoneamine or TAA), ammonia and hydrogen using cobalt or nickel catalysts on a support material.

2. Discussion of the Background

TAA can be converted into TAD by aminating hydrogenation. In the conventional procedure, the corresponding imine is first formed from TAA and $NH_3$ in a first step with elimination of water, with the imine then being reacted. These reactions proceed in a single-stage process, with pressures of 15–100 bar and temperatures of 100°–140° C. usually being necessary. Cobalt or nickel catalysts are usually used. A further requirement of these known processes is the necessity of performing the reactions in a solvent which doesn't participate in the reaction as a reactant.

TAD is used as an intermediate in the synthesis of HALS products (Hindered Amine Light Stabilizers).

Known methods for the large scale preparation of TAD from TAA use Raney nickel (SU 1033169) or Raney cobalt (J6 1088304) as catalyst and are, without exception, carried out using a solvent which is to be additionally introduced, usually methanol (examples in J6 2016461 and J6 1033169). In addition, a significant molar excess of ammonia is always necessary for the reaction according to these processes.

The procedures of the prior art using an added solvent such as methanol or water, result in a lower degree of reactor utilization, plus complicated and expensive additional steps for the later separation and removal of the solvent. In the case of organic solvents (such as methanol), the starting material costs can be considerable, as well as the increased hazard potential, due to increased risk of exposure or fire.

The amounts of catalyst used in the processes of the prior art are sometimes up to 10% (example in GB 2176473) of the amount of starting material (TAA) and result in correspondingly increased costs.

The required high excesses of ammonia lead to work-up steps having increased energy expense in the recovery of the excess ammonia and thus reduce the usable reactor volume for the starting material (TAA).

SUMMARY OF THE INVENTION

Accordingly, one object of the present invention is to provide a method for the preparation of TAD from TAA, which increases the space-time yield of the reactor by essentially complete omission of any added solvent.

A further object of the present invention is to provide a method for preparing TAD from TAA which allows a reduction in the amount of catalyst needed.

A further object of the present invention is to provide a method for preparing TAD from TAA which minimizes the amount of ammonia needed.

A further object of the present invention is to provide a method for preparing TAD from TAA which provides each of the above advantages without significantly impairing the product quality.

These and other objects of the present invention have been satisfied by the discovery of a substantially solvent-free method for preparing TAD from TAA comprising contacting a mixture of 2,2,6,6-tetramethylpiperidone (TAA), ammonia and hydrogen, with a supported cobalt or nickel catalyst in the substantial absence of any added solvent.

DETAILED DESCRIPTION OF THE PREFERRED EMBODIMENTS

The present invention relates to a substantially solvent-free process for preparing 4-amino-2,2,6,6-tetramethylpiperidine from 2,2,6,6-tetramethylpiperidone, ammonia and hydrogen, wherein the reactants are contacted with a supported cobalt or nickel catalyst in the substantial absence of a solvent. With respect to the present invention, the phrase "substantial absence of solvent" is intended to limit the maximum allowable added solvent to no more than 5% of the total reaction volume, preferably $\leq 1\%$, most preferably 0%.

The absence of any added solvent in the present process reduces starting material costs, reduces distillation costs and increases the space-time yield of the reactor, since the entire reactor volume can be filled with the reaction mixture and hence the desired product. Furthermore, while the prior art processes used a molar excess of ammonia ($NH_3$):TAA=2.1 to 2.75:1 (see Example in GB 2176473 and J6 2016461) the molar ratio of $NH_3$:TAA in the present process can be reduced to much lower values, if desired. The molar ratio of $NH_3$:TAA is preferably from 1:1 to 5:1, most preferably from 1:1 to 2:1.

By reducing the amount of ammonia needed, the present process reduces starting material costs, reduces work-up costs for ammonia recovery and further increases the space-time yield of product.

The catalyst concentration used in the present process is from 0.05 to 1%, preferably from 0.05 to 0.2%, by weight based on 2,2,6,6-tetramethylpiperidone (TAA) used. The calculation of % catalyst is based on the metal content of the supported catalyst. The support for the present catalysts can be any conventional support used in the catalyst art which has no detrimental effect on the metal catalyst itself. Preferred supports include aluminum oxide, silicon dioxide or zinc oxide. Reducing the amount of catalyst also reduces the production costs in the process of the present invention.

The temperature in the hydrogenative amination process of the present invention is from 50° to 200° C., with a temperature of from 80° to 150° C. being preferred. Particular preference is given to a temperature of from 100° to 130° C. The pressure in the hydrogenative amination is from 10 to 300 bar, preferably from 50 to 200 bar. Particular preference is given to a pressure of from 80 to 150 bar.

Having generally described this invention, a further understanding can be obtained by reference to certain specific examples which are provided herein for purposes of illustration only and are not intended to be limiting unless otherwise specified.

EXAMPLES

Example 1

3100 kg of TAA (=20 kmol) were introduced into a clean, dry reactor which had been previously flushed with nitrogen. 5.8 kg of cobalt catalyst RCH 45/20 from Ruhrchemie (0.19% of total catalyst based on TAA. Since the cobalt concentration of the catalyst was 48%, 5.8 kg ×0.48=2.8 kg of cobalt, corresponding to 0.09% of cobalt based on TAA used) were added and the mixture homogenized. Subsequently, liquid ammonia was added (540 kg=31.8 kmol), the mixture heated to 120° C. and the reactor pressurized with hydrogen to 95 bar. After a reaction time of 2.5–3 hours at 120° C. (removal of heat is necessary), the reaction was complete. The contents of the reactor were cooled and depressurized. This gave TAD having a purity of 96–97%. The work-up was carried out using conventional purification procedures, such as distillation.

Example 2

310 g of TAA (=2 mol) were introduced into a clean, dry reactor which had been previously flushed with nitrogen. 0.58 g of cobalt catalyst RCH 45/20 from Ruhrchemie (0.19% of 5 total catalyst based on TAA. Since the cobalt concentration of the catalyst is 48%, 0.58 g ×0.48=0.28 g of cobalt, corresponding to 0.09% of cobalt based on TAA used) was added and the mixture stirred. Subsequently, liquid ammonia was added (46.5 g=2.74 mol), the mixture heated to 120° C. and the reactor pressurized with hydrogen to 95 bar. After a reaction time of 6 hours at 120° C. (removal of heat is necessary), the reaction was complete. The autoclave was then cooled and depressurized to give TAD having a purity of 95%. Conventional work-up procedures were used to purify the product.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. In a process for preparing 4-amino-2,2,6,6-tetramethylpiperidine (TAD) contacting a mixture of 2,2,6,6-tetramethylpiperidone (TAA), ammonia and hydrogen with a supported cobalt or nickel catalyst, the improvement being preparing in the substantial absence of any added solvent.

2. The process according to claim 1, wherein ammonia and TAA are present in a molar ratio of ammonia:TAA of from 1:1 to 5:1.

3. The process according to claim 1, wherein ammonia and TAA are present in a molar ratio of ammonia:TAA of from 1:1 to 2:1.

4. The process according to claim 1, wherein the supported cobalt or nickel catalyst is present in an amount of from 0.05 to 1%, calculated on % cobalt or nickel metal contained therein and based on TAA used.

5. The process according to claim 1, wherein the supported cobalt or nickel catalyst is present in an amount of from 0.05 to 0.2% calculated on % cobalt or nickel metal contained therein and based on TAA used.

6. The process according to claim 1, wherein the process is conducted at a temperature of from 50° to 200° C.

7. The process according to claim 1, wherein the process is conducted at a temperature of from 80° to 150° C.

8. The process according to claim 1, wherein the process is conducted at a pressure of from 10 to 300 bar.

9. The process according to claim 1, wherein the process is conducted at a pressure of from 50 to 200 bar.

10. The process according to claim 1, wherein the process is conducted at a pressure of from 80 to 150 bar.

11. The process of claim 1, wherein said supported cobalt or nickel catalyst comprises a cobalt or nickel composition on a support selected from the group consisting of aluminum oxide, silicon dioxide and zinc oxide.

* * * * *